(12) United States Patent
Racz et al.

(10) Patent No.: US 9,539,415 B2
(45) Date of Patent: Jan. 10, 2017

(54) CATHETERS INCLUDING BEND INDICATORS, CATHETER ASSEMBLIES INCLUDING SUCH CATHETERS AND RELATED METHODS

(75) Inventors: N. Sandor Racz, Coppell, TX (US); Gabor J. Racz, Dallas, TX (US)

(73) Assignee: Custom Medical Applications, Inc., Johnstown, NY (US)

( * ) Notice: Subject to any disclaimer, the term of this patent is extended or adjusted under 35 U.S.C. 154(b) by 0 days.

(21) Appl. No.: 14/369,172

(22) PCT Filed: Dec. 28, 2011

(86) PCT No.: PCT/US2011/067638
§ 371 (c)(1),
(2), (4) Date: Jun. 26, 2014

(87) PCT Pub. No.: WO2013/100987
PCT Pub. Date: Jul. 4, 2013

(65) Prior Publication Data
US 2015/0094685 A1    Apr. 2, 2015

(51) Int. Cl.
*A61M 25/01* (2006.01)
*A61M 25/00* (2006.01)

(52) U.S. Cl.
CPC ..... *A61M 25/0152* (2013.01); *A61M 25/0012* (2013.01); *A61M 25/0074* (2013.01);
(Continued)

(58) Field of Classification Search
CPC ................ A61B 17/3401; A61B 2017/00331; A61M 2025/0007; A61M 25/0108; A61M 25/0012; A61M 25/0074; A61M 2025/0008; A61M 25/0152
See application file for complete search history.

(56) References Cited

U.S. PATENT DOCUMENTS

| 4,586,923 A | 5/1986 | Gould et al. |
| 4,834,709 A * | 5/1989 | Banning ........... A61M 25/0041 604/170.02 |

(Continued)

FOREIGN PATENT DOCUMENTS

| WO | 2006110554 A2 | 10/2006 |
| WO | 2011103530 A2 | 8/2011 |
| WO | 2013100987 A1 | 7/2013 |

OTHER PUBLICATIONS

PCT International Search Report, PCT/US2011/067638, dated Sep. 10, 2012.
(Continued)

*Primary Examiner* — Bradley Osinski
(74) *Attorney, Agent, or Firm* — TraskBritt

(57) ABSTRACT

Epidural catheters include a tubular member and at least one bend indicator located proximate a distal end of the tubular member to provide a reference point for a user to bend the catheter. Catheter assemblies may include such catheters. Methods of inserting an epidural catheter having a bent distal end into a patient include bending a catheter at a location proximate at least one bend indicator formed proximate a distal end of the catheter and inserting at least a portion of the catheter into a patient. Methods of making an epidural catheter include forming a tubular member having a proximal end and a distal end and forming at least one bend indicator on the catheter proximate the distal end of the tubular member to provide a reference point for a user to bend the catheter.

9 Claims, 3 Drawing Sheets

(52) U.S. Cl.
CPC .. *A61M 25/0108* (2013.01); *A61B 2090/0811* (2016.02); *A61M 2025/0007* (2013.01); *A61M 2025/0008* (2013.01); *Y10T 29/49826* (2015.01)

(56) References Cited

U.S. PATENT DOCUMENTS

| | | | |
|---|---|---|---|
| 4,943,278 A | | 7/1990 | Euteneuer et al. |
| 4,983,169 A | * | 1/1991 | Furukawa ......... A61M 25/0054 604/164.13 |
| 5,069,674 A | * | 12/1991 | Fearnot et al. ............... 604/524 |
| 5,195,979 A | | 3/1993 | Schinkel et al. |
| 6,036,682 A | * | 3/2000 | Lange et al. .................. 604/529 |
| 6,272,370 B1 | * | 8/2001 | Gillies et al. .................. 600/411 |
| 6,562,049 B1 | * | 5/2003 | Norlander et al. ........... 606/108 |
| 6,997,941 B2 | | 2/2006 | Sharkey et al. |
| 7,022,109 B1 | * | 4/2006 | Ditto ............................. 604/158 |
| 7,195,614 B2 | | 3/2007 | Geisler et al. |
| 7,601,138 B2 | | 10/2009 | Goebel et al. |
| 8,038,667 B2 | | 10/2011 | Racz et al. |
| 8,088,119 B2 | | 1/2012 | Saal et al. |
| 2004/0181207 A1 | | 9/2004 | Vitullo et al. |
| 2005/0167436 A1 | | 8/2005 | Adam |
| 2006/0167436 A1 | | 7/2006 | Geisler |
| 2007/0055204 A1 | | 3/2007 | Geisler et al. |
| 2007/0073269 A1 | | 3/2007 | Becker |
| 2008/0188826 A1 | | 8/2008 | Saal et al. |
| 2008/0188827 A1 | | 8/2008 | Saal et al. |
| 2008/0195041 A1 | | 8/2008 | Goldfarb et al. |
| 2009/0187140 A1 | * | 7/2009 | Racz ................. A61M 25/0606 604/41 |
| 2009/0192496 A1 | | 7/2009 | Suwito et al. |
| 2010/0179562 A1 | | 7/2010 | Linker et al. |
| 2010/0292687 A1 | | 11/2010 | Kauphusman et al. |
| 2011/0264217 A1 | | 10/2011 | Qureshi |
| 2011/0306879 A1 | | 12/2011 | Saal et al. |

OTHER PUBLICATIONS

PCT Written Opinion, PCT/US2011/067638 dated Sep. 10, 2012.
PCT International Search Report, PCT/US2011/067638, dated Jul. 10, 2014.

* cited by examiner

CATHETERS INCLUDING BEND INDICATORS, CATHETER ASSEMBLIES INCLUDING SUCH CATHETERS AND RELATED METHODS

CROSS-REFERENCE TO RELATED APPLICATIONS

This application is a national phase entry under 35 U.S.C. §371 of International Patent Application PCT/US2011/067638, filed Dec. 28, 2011, designating the United States of America and published in English as International Patent Publication WO 2013/100987 A1 on Jul. 4, 2013, the disclosure of which is hereby incorporated herein in its entirety by this reference.

TECHNICAL FIELD

The disclosure relates generally to medical devices such as catheters. More specifically, embodiments of the disclosure relate to epidural catheters including one or more bends indicators on the catheter at or near a distal end of the catheter.

BACKGROUND

During insertion and placement of a conventional catheter, it may be desirable to control (e.g., steer) the catheter in a selected direction. For example, a needle, sometimes referred to in the art as a "cannula," may puncture the skin of a patient and be inserted to an initial penetration depth. A catheter, typically reinforced by a stylet inserted within the catheter, may be introduced into the patient through the needle. The distal end of the catheter may then be advanced into the patient beyond the tip of the needle toward a desired destination, such as, for example, a location within the epidural space where it is desired to administer an analgesic. Upon exiting the needle, the ability to control the direction in which the distal end of the catheter proceeds may be necessary to prevent damaging sensitive tissues and neural structures through unintended contact with the distal end of the catheter, to prevent mistaken administration of medications with unintended effect, and otherwise prevent harm to the patient. U.S. Pat. No. 7,601,138 B2, issued Oct. 13, 2009 to Goebel et al., discloses that the tip of a cannula may include a bend to bias advancement of the catheter inserted therethrough in a desired direction. Alternatively, it is known in the art that a user (e.g., a doctor or other medical personnel) may bend (i.e., plastically deform) the catheter at a location near the distal end. The user may then steer the catheter in a desired direction by twisting an external portion thereof, causing the distal end to point in a known direction due to the bend placed near the distal end of the catheter.

DISCLOSURE

In some embodiments, the present disclosure includes catheters having a tubular member including a distal end and at least one bend indicator located proximate the distal end of the tubular member to provide a reference point for a user to bend the catheter.

In some embodiments, the catheter may include a coiled member extending from within the tubular member beyond the distal end of the tubular member to form a tip of the catheter.

In additional embodiments, the present disclosure includes catheter assemblies including a catheter as described above.

In yet additional embodiments, the present disclosure includes a method of inserting a catheter having a bent distal end into a patient. The method including bending a catheter at a location proximate at least one bend indicator formed proximate a distal end of the catheter and inserting at least a portion of the catheter into a patient.

In yet additional embodiments, the present disclosure includes a method of making a catheter. The method including forming a tubular member having a proximal end and a distal end and forming at least one bend indicator on the catheter proximate the distal end of the tubular member to provide a reference point for a user to bend the catheter.

DETAILED DESCRIPTION

The drawings are not necessarily to scale and relative dimensions may have been exaggerated for the sake of clarity. Additionally, elements common between figures may retain the same or similar numerical designation.

Figure 1:
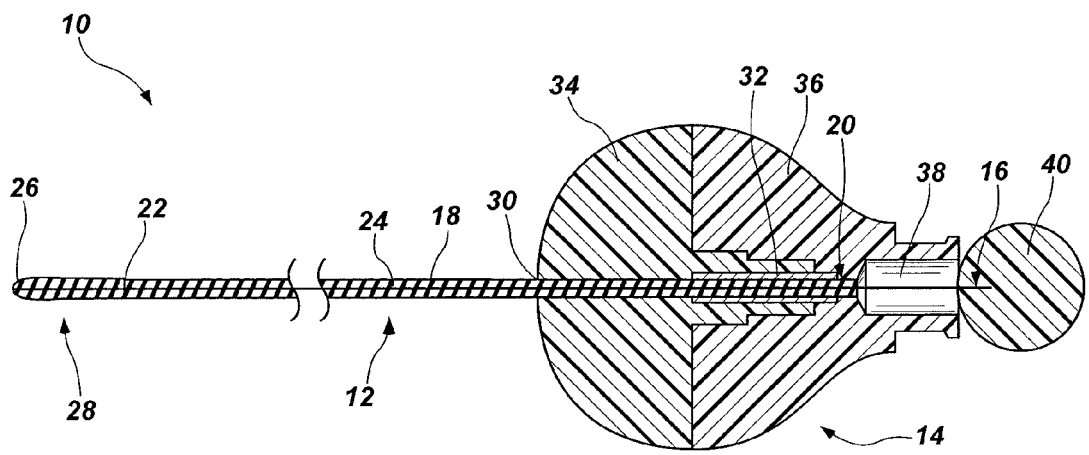
FIG. 1 is a cross-sectional view of a catheter assembly in accordance with an embodiment of the present disclosure.
Figure 2:
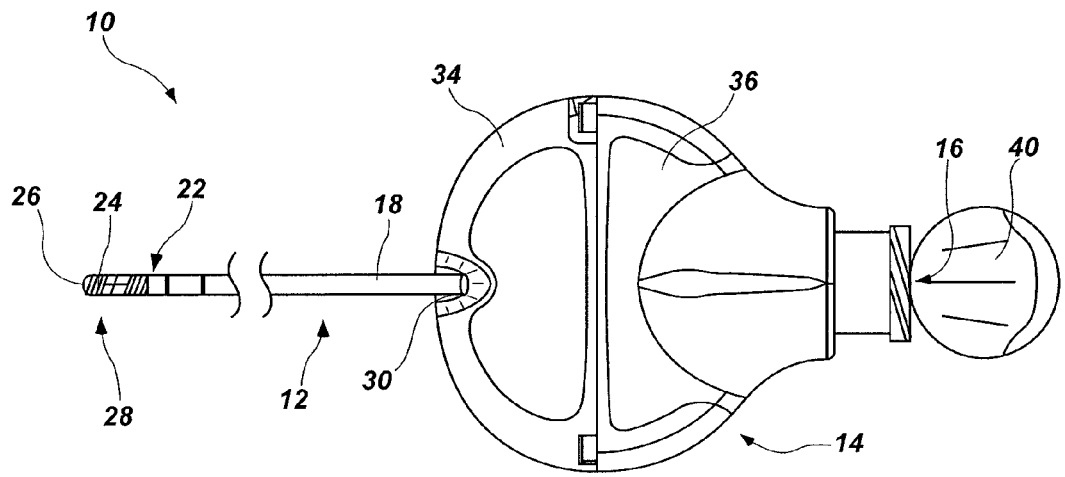
FIG. 2 is a plan view of the catheter assembly shown in FIG. 1.

Referring to FIGS. 1 and 2, a cross-sectional view and a plan view of a catheter assembly 10 are shown, respectively. The catheter assembly 10 includes a catheter 12, a catheter hub 14, and a stylet 16. The catheter 12 comprises a tubular member 18 having a proximal end 20 and a distal end 22. The tubular member 18 typically comprises a flexible material, such as, for example, a polymer suitable for use in medical applications. In some embodiments, the catheter 12 may include a coiled member 24 positioned in the catheter 12 to, for example, reinforce the catheter 12 and reduce its propensity to restrict flow when bent (i.e., kinked). In some embodiments, the coiled member 24 may extend from within the tubular member 18 beyond the distal end 22 of the tubular member 18 to form a tip 26 of the catheter 12 at the distal end 28 thereof. In other embodiments, the tip 26 of the catheter 12 may be forming by another portion of the catheter 12 (e.g., by the distal end 22 of the tubular member 18). The coiled member 24 may be formed as a spring disposed within the tubular member 18 and extending beyond the distal end 22 of the tubular member to form a distal end 28 of the catheter 12. At least some of the coils of the coiled member 24 are spaced further apart at the distal end 28 of the catheter 12 near the tip 26 to enable a fluid (e.g., a liquid analgesic) to exit the catheter 12 at the distal end 28 thereof. In some embodiments, an end of the coiled member 24 forming the tip 26 may include a substantially smooth end (e.g., a semispherical outer surface).

Figure 3:
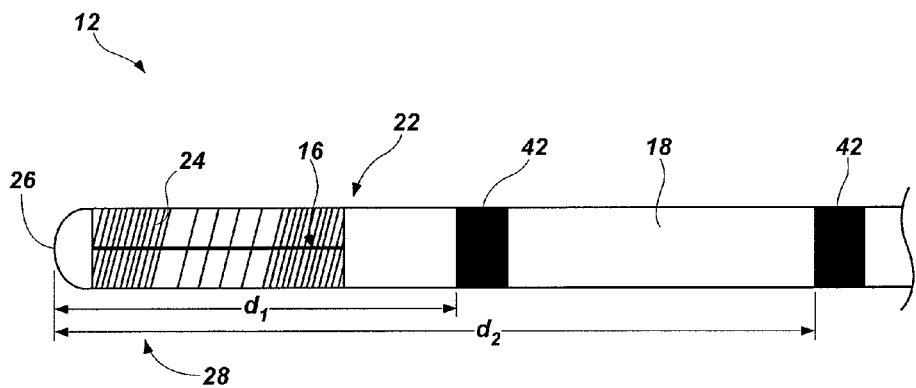
FIG. 3 is an enlarged view of a distal end of the catheter shown in FIG. 1.

In some embodiments, the stylet 16 may be inserted into the catheter 12 to reinforce the catheter 12, for example, during insertion and placement. For example, the stylet 16 may be inserted within the catheter 12 and bent in unison with the catheter 12 to enable the catheter 12 to remain in the bent configuration during a procedure. The stylet 16 extends from a stylet cap 40 toward the distal end 28 of the catheter 12. The stylet 16 typically comprises an elongated member configured to increase stiffness and structural strength of the catheter 12 in which the stylet 16 may be inserted and, when bent along with the catheter 12, will act to maintain the catheter 12 in a bent configuration. In some embodiments, the stylet 16 may extend at least to bend indicators 42 (FIG. 3). For example, the stylet 16 may extend to at least the distal end 22 of the catheter 12 (e.g., to the tip 26). The stylet 16 may comprise a wire, a tube, a plurality of intertwined or interwoven wires, or a plurality of intertwined or interwoven tubes. In some embodiments, the stylet 16 optionally includes at least one of enhanced radio frequency (RF), resistance heating, thermocouple, and microwave apparatus. The stylet 16 is formed from a material suitable for use in medical fields, such as, for example, medical grade stainless steel or medical grade titanium.

In some embodiments, the proximal end 20 of the catheter 12 may be secured within the catheter connection hub 14. Exemplary catheter connection hubs 14 for connection to catheters 12 are disclosed in, for example, U.S. Patent Application Publication No. 2008/0183154, published Jul. 31, 2008, now U.S. Pat. No. 8,038,667, issued Oct. 18, 2011, to Racz et al. The proximal end 20 of the catheter 12 is configured for insertion into a catheter-receiving portion 30 of the catheter connection hub 14. The proximal end 20 of the catheter 12 is securable within the catheter-receiving portion 30 of the catheter connection hub 14 using, for example, a deformable member 32 that may selectively constrict and expand in response to relative rotation of first and second portions 34 and 36 of the catheter connection hub 14. Such selective constriction and expansion of the deformable member 32 selectively secures and releases the proximal end 20 of the catheter 12. The catheter connection hub 14 typically includes a connection portion 38 (e.g., a female Luer taper portion) at an end of the catheter connection hub 14 opposing the catheter-receiving portion 30 for connection to a fluid source. The connection portion 38 extends within the catheter connection hub 14 to a location at or near a terminal end of the catheter-receiving portion 30.

In use, the catheter connection hub 14 is connected to the proximal end 20 of the tubular member 18 of the catheter 12 after the distal end 28 of the catheter 12 has been placed at what the doctor or other medical care personnel thinks is an appropriate location within the patient. Once the catheter connection hub 14 has been secured to the proximal end 20 of the tubular member 18 of the catheter 12, another device or substance (e.g., an RF probe or a fluid analgesic) may be introduced to the patient through the catheter. For example, a hypodermic syringe comprising a male Luer taper portion and containing a fluid analgesic may be inserted into the catheter 12 through the connection portion 38 of the catheter connection hub 14, and the fluid analgesic may be introduced to the patient through the catheter 12. Afterward, the catheter connection hub 14 typically remains connected to the catheter 12 for additional administrations of the other device or substance or during repositioning of the distal end 28 of the catheter 12. For example, the catheter connection hub 14 may remain fixed to the proximal end 20 of the tubular member 18 of the catheter 12 and may be affixed to the skin of the patient, such as with medical tape, to allow for additional doses of fluid analgesic to be supplied through the catheter 12 as previously described.

Referring to FIG. 3, an enlarged view of the distal end 28 of the catheter 12 of FIG. 1 is shown. The catheter 12 includes one or more bend indicators 42 located proximate to the distal end 22 of the tubular member 18. It is noted that while the embodiment of FIG. 3 illustrates the catheter 12 having two bend indicators 42, it is contemplated the catheter 12 may include any number of bend indicators 42 (e.g., one, three, four, five, or more). The bend indicators 42 are formed as visible markings that provide a reference point for a user to bend the catheter 12 (e.g., the tubular member 18 and the coiled member 24 and stylet 16, if implemented) prior to insertion and placement of the catheter 12. In other words, the bend indicators 42 may be utilized to form a portion of the catheter 12 that extends at an oblique angle relative to an immediately adjacent portion of the catheter 12. The bend indicators 42 may be substantially consistently formed on a plurality of catheters 12 such that bending each catheter 12 at the same location relative to the bend indicators 42 will provide a consistent location of the bend on each of the catheters 12. In some embodiments, the presence of bend indicators 42 on a catheter 12 may signal to a user that the procedure to be performed (e.g., a catheter insertion procedure) may require that or may be more easily performed when the distal end 28 of the catheter 12 is bent.

The bend indicators 42 are located at a distance from the tip 26 of the catheter 12 where it may be desirable to bend the catheter 12 for a particular procedure. For example, a first bend indicator 42 may be located a first distance $d_1$ from the tip 26 of the catheter 12. The first distance $d_1$ may correspond to a location for a bend that may be used during a procedure that requires maneuvering the distal end 28 of the catheter 12 within a relatively tight space. For example, the first distance $d_1$ may correspond to a location for a bend used when positioning the distal end 28 of the catheter 12 within the cervical or upper thoracic regions of the spine for administration of an analgesic. Such a first distance $d_1$ may be about 15 mm from the tip 26 of the catheter 12. For example, the first distance may be 15 mm±2 mm, 15 mm±1 mm, or 15 mm±0.5 mm from the tip 26 of the catheter 12. A second bend indicator 42 may be located a second distance $d_2$ from the tip 26 of the catheter 12. The second distance $d_2$ may correspond to a location for a bend used during a procedure that requires maneuvering the distal end 28 of the catheter 12 within a relatively less tight space. For example, the second distance $d_2$ may correspond to a location for a bend used when positioning the distal end 28 of the catheter 12 within the lumbar or sacral region of the spine for administration of an analgesic. Such a second distance $d_2$ may be about 25 mm from the tip 26 of the catheter 12. For example, the second distance $d_2$ may be 25 mm±2 mm, 25 mm±1 mm, or 25 mm±0.5 mm from the tip 26 of the catheter 12.

In embodiments where the bend indicators 42 are located at first and second distances $d_1$ and $d_2$ on a single catheter 12, the bend indicators 42 may enable a single catheter 12 to be used for either type of procedure described previously. In other embodiments, a single bend indicator 42 may be located at either the first distance $d_1$ or the second distance $d_2$ on a single catheter 12. In such an embodiment, a catheter 12 may be specifically designated for one of the procedures described previously. In this way, the presence of a single bend indicator 42 may signal to a user that the catheter 12 should be bent before performing the procedure and may signal which procedure is to be performed or what procedure the catheter is specifically designed to perform.

The bend indicators 42 may be formed on a portion of the catheter 12. For example, the bend indicators 42 may be printed or otherwise marked on a portion of the tubular member 18 (e.g., an external portion). In other embodiments, the bend indicators 42 may be formed on other portions of the catheter 12 such as on the coiled spring 24 or the stylet 16, where implemented. The bend indicators 42 typically comprise a material that provides a visible contrast with the material of the tubular member 18, is suitable for medical applications, and is not easily removed from the tubular member 18. In embodiments where the material of the catheter 12 is translucent or transparent, the bend indicators 42 may alternatively be printed on an internal portion of the tubular member 18. In further embodiments, the bend indicators 42 are integrally formed with the tubular member 18 of the catheter 12. For example, a pigment or dye added to the material of the tubular member 18 of the catheter 12 forms the bend indicators 42. In other embodiments, the bend indicators 42 may comprise a different material embedded within or otherwise connected to the material of the tubular member 18 of the catheter 12. In some embodiments, the bend indicators 42 may be formed from a radio-opaque material (i.e., a material that prevents or distorts passage of electromagnetic radiation, such as X-rays), such as, for example, barium or iodine. In such embodiments, the bend indicators 42 enable a user to verify that the distal end 28 of the catheter 12 has been properly placed within the patient using electromagnetic imaging, such as X-ray imaging.

Figure 4:
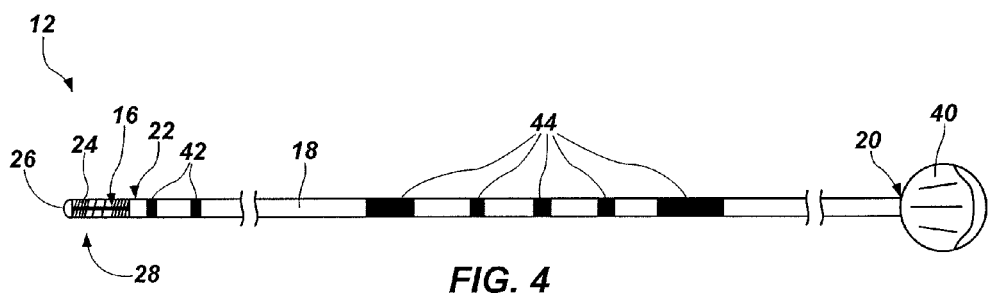
FIG. 4 is a plan view of a catheter in accordance with another embodiment of the present disclosure.

Referring to FIG. 4, a plan view of a catheter 12 is shown. The catheter 12 comprises a tubular member 18 extending from a proximal end 20 to a distal end 22. As shown in FIG. 4, the catheter 12 includes a coiled member 24 extending from within the tubular member 18 beyond the distal end 22 to a tip 26. The catheter 12 includes at least two bend indicators 42 located proximate the distal end 22 of the tubular member 18 to provide a reference point for a user to bend the tubular member 18 and coiled member 24. A first of the bend indicators 42 is located about 15 mm from the tip 26 of the coiled member 24, and a second of the bend indicators 42 is located about 25 mm from the tip 26 of the coiled member 24, as discussed above. The catheter 12 also includes an optional plurality of depth indicators 44 located between the bend indicators 42 and the proximal end 20 of the tubular member 18. The depth indicators 44 are configured to indicate to a user the depth of insertion of the distal end 28 of the catheter, and are typically located a positions corresponding to depths of insertion for certain procedures (e.g., depths relative to a flexible introducer cannula (FIC)). The depth indicators 44 are located approximately at a midpoint between the distal end 28 of the catheter 12 and the proximal end 20 of the tubular member 18 of the catheter 12 in some embodiments. In other embodiments, the depth indicators 44 are located proximate the proximal end 20 of the tubular member 18 of the catheter 12. The catheter 12 may include a stylet 16 inserted therein and extending from a stylet cap 40 toward the distal end 28 of the catheter 12. After being provided with a catheter 12, a user wishing to control the direction in which the catheter 12 advances during insertion and placement of the catheter 12 bends the catheter 12.

Figure 5:
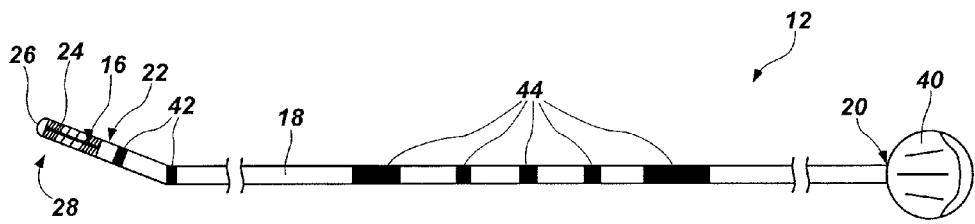
FIG. 5 is a plan view of the catheter of FIG. 4 after the catheter has been bent.

Referring to FIG. 5, a plan view of the catheter 12 of FIG. 4 is shown after it has been bent. The user bends a portion of the catheter 12 (e.g., the tubular member 18, the coiled member 24, and the stylet 16 inserted therein) causing at least some plastic deformation to the portion of the catheter 12 at a location proximate to one or more of the bend indicators 42. For example, a user may bend the catheter 12 at or near one of the bend indicators 42. In some embodiments, the bend indicators 42 may enable a user to be instructed to bend the catheter 12 at or near one or more of the bend indicators 42, for example, during training to ensure that the catheter 12 is inserted and placed properly for a selected procedure. In such an embodiment, the bend indicators 42 enable a user to relatively more accurately and consistently locate the bend on the catheter 12 to ensure that procedures using the bent catheter 12 are properly performed. As another example, a user may bend the catheter 12 at a location near the bend indicators 42. An experienced user may find that bending the catheter 12 at a location not precisely at, but nonetheless near, the bend indicators 42 may be preferable to that user for a selected procedure. In such situations, the bend indicators 42 serve as reference points to enable experienced users to accurately and consistently locate the bend on the catheter 12 to ensure that procedures using the bent catheter are properly and consistently performed. In other words, the bend indicators 42 may enable a user to repeatedly bend multiple catheters 12 in consistent locations. By way of example, the user may bend the catheter 12 at a location within 5 mm from one of the bend indicators 42, within 2 mm from one of the bend indicators 42, or within 1 mm from one of the bend indicators 42. As specific, non-limiting examples, a user may bend the catheter 12 at a location about 15 mm from the tip 26 of the coiled member 24 when placing the distal end 28 of the catheter 12 in the cervical or upper thoracic region of the epidural space or a user may bend the catheter 12 at a location about 25 mm from the tip 26 of the coiled member 24 when placing the distal end 28 of the catheter 12 in the lumbar or sacral region of the epidural space. By indicating to a user where a bend may be consistently and accurately placed on a catheter 12, the bend indicators 42 enable the bent catheter 12 to operate in a consistent, predictable fashion, which enables the user to consistently and reliably perform a selected procedure.

Figure 6:
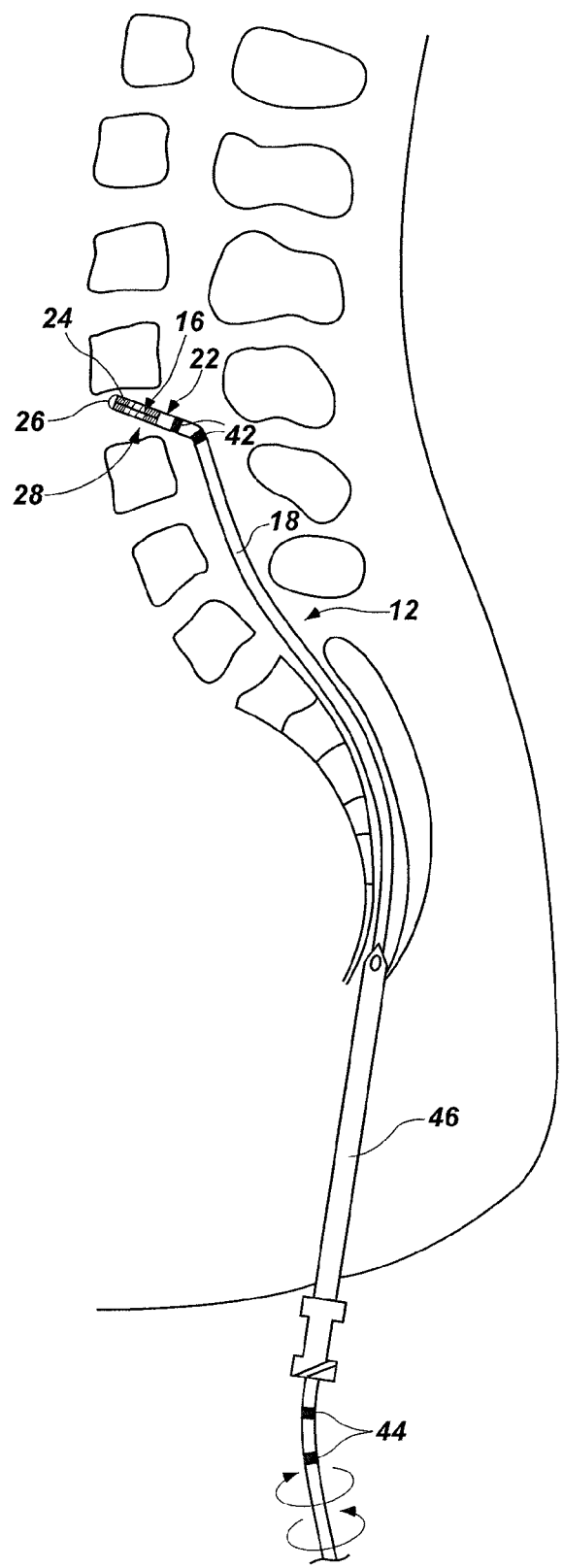
FIG. 6 is a simplified partial cross-sectional view of the catheter of FIG. 5 during insertion and placement.

Referring to FIG. 6, a simplified partial cross-sectional view of the catheter 12 of FIG. 5 is shown during insertion and placement. After bending the catheter 12, a user inserts the catheter 12 into a patient to perform a selected procedure. For example, a user may insert the catheter 12 into the patient using the so-called "Racz method" of entering the epidural space through the coccyx. In such a method, a user typically punctures the skin of the patient using a needle 46 and inserts the needle 46 to a first insertion depth. The bent catheter 12 is inserted into the patient through the needle 46, and beyond the first insertion depth. A user then controls the direction in which the tip 26 of the catheter 12 advances by controlling rotation of the catheter 12 (e.g., torque applied to the catheter 12) at the exterior of the patient. For example, a user may control the direction in which the distal end 28 of the catheter 12 advances by rotating the catheter 12 in a clockwise or counterclockwise direction, as indicated by arrows in FIG. 6. As the user rotates the catheter 12, the bend proximate the distal end 28 of the catheter 12 causes the distal end 28 of the catheter to point, and therefore proceed, in a different direction than when the catheter 12 has not been rotated. As another example, a user controls the direction in which the distal end 28 of the catheter 12 advances by retaining the catheter 12 in a fixed radial orientation (i.e., prevents rotation of the catheter 12). In such a method, a user may ensure that a catheter 12 already proceeding in a desired direction maintains its course. Should the user determine that the distal end 28 of the catheter 12 is veering off course or has advanced to an undesirable location, the user may rotate the catheter 12 while altering the depth of insertion of the catheter to reposition or course-correct. In such a method, the user may control the direction in which the distal end 28 of the catheter 12 advances during insertion, placement, and repositioning of the distal end 28 of the catheter 12.

What is claimed is:

1. A method of inserting an epidural catheter having a bent distal end into a patient, the method comprising:
   providing an epidural catheter assembly to an end user in an unbent state comprising:
   a tubular member comprising a distal end;
   at least two bend indicators located proximate the distal end of the tubular member to provide reference points for the end user to bend at least a portion of the catheter assembly, each bend indicator of the at least two bend indicators located at a select distance from a tip of the catheter assembly to provide a respective reference point for the end user to bend a portion of the catheter assembly, the at least two bend indicators comprising a first bend indicator and a second bend indicator;
   inserting a stylet at least partially into the catheter assembly;
   after inserting the stylet at least partially into the catheter assembly, bending, by the end user, at least a portion of the catheter assembly at the first bend indicator or at the second bend indicator; and
   after bending the at least a portion of the catheter assembly and plastically deforming the stylet within the catheter assembly, inserting, by the end user, the at least a portion of the catheter assembly into the patient into the cervical or upper thoracic region of the patient's spine for administration of an analgesic if the catheter assembly was bent at the first bend indicator or into the lumbar or sacral region of the patent's spine for administration of the analgesic if the catheter assembly was bent at the second bend indicator.

2. The method according to claim 1, wherein providing the epidural catheter assembly comprises providing a first bend indicator located about fifteen (15) mm from the tip of the catheter assembly to position the distal end of the catheter assembly in one of a cervical region and an upper thoracic region of the patient's spine.

3. The method according to claim 2, wherein providing the epidural catheter assembly further comprises providing a second bend indicator located about twenty-five (25) mm from the tip of the catheter assembly to position the distal end of the catheter assembly in one of a lumbar region and a sacral region of the patient's spine.

4. The method according to claim 1, further comprising controlling a direction of the tip of the catheter assembly as the catheter assembly advances into the patient by controlling rotation of the catheter assembly.

5. The method according to claim 4, wherein controlling a direction of the tip of the catheter assembly as the catheter assembly advances into the patient comprises rotating the catheter assembly.

6. The method according to claim 4, wherein controlling a direction of the tip of the catheter assembly as the catheter assembly advances into the patient comprises retaining the catheter assembly in a fixed radial orientation.

7. A method of inserting a catheter having a bent distal end into a subject proximate the subject's nervous system, the method comprising:
   providing a catheter assembly to an end user, wherein a distal portion of a tubular member for supplying a treatment to the subject of the catheter assembly is in a substantially unbent configuration, the catheter including at least two bend indicators comprising a first bend indicator and a second bend indicator;
   inserting a stylet at least partially into the catheter assembly;
   after inserting the stylet at least partially into the tubular member, bending, by the end user, at least the distal portion of the tubular member of the catheter assembly at the first bend indicator or at the second bend indicator, wherein each bend indicator of the at least two bend indicators is located at a select distance from a tip of the catheter assembly to provide a respective reference point for the end user to bend the distal portion of the catheter assembly, the bending further comprising plastically deforming the stylet within the tubular member to reinforce the bent distal portion of the tubular member; and
   after bending the at least the distal portion of the tubular member and plastically deforming the stylet within the tubular member, inserting, by the end user, the at least a portion of the catheter assembly into the patient into the cervical or upper thoracic region of the patient's spine for administration of an analgesic if the catheter assembly was bent at the first bend indicator or into the lumbar or sacral region of the patent's spine for administration of the analgesic if the catheter assembly was bent at the second bend indicator.

8. The method according to claim 7, wherein providing the catheter assembly comprises providing a first bend indicator of the at least two bend indicators on the tubular member located about fifteen (15) mm from the tip of the catheter assembly adapted for maneuvering the distal end of the tubular member within a cervical or upper thoracic region of the subject's spine for administration of an analgesic.

9. The method according to claim 8, wherein providing the catheter assembly comprises providing a second bend indicator of the at least two bend indicators on the tubular member located about twenty-five (25) mm from the tip of the catheter assembly adapted for maneuvering the distal end of the tubular member within the lumbar or sacral region of the subject's spine for administration of the analgesic.

* * * * *